United States Patent
Pressacco

(10) Patent No.: US 10,092,406 B2
(45) Date of Patent: Oct. 9, 2018

(54) ACETABULAR PROSTHESIS AND CORRESPONDING METHOD FOR PRODUCTION AND ASSEMBLY

(71) Applicant: LIMACORPORATE SPA, San Daniele del Friuli (IT)

(72) Inventor: Michele Pressacco, Udine (IT)

(73) Assignee: LIMACORPORATE SPA, San Daniele del Friuli (IT)

( * ) Notice: Subject to any disclaimer, the term of this patent is extended or adjusted under 35 U.S.C. 154(b) by 0 days.

(21) Appl. No.: 14/438,602

(22) PCT Filed: Oct. 24, 2013

(86) PCT No.: PCT/IB2013/002378
§ 371 (c)(1),
(2) Date: Apr. 24, 2015

(87) PCT Pub. No.: WO2014/064515
PCT Pub. Date: May 1, 2014

(65) Prior Publication Data
US 2015/0257887 A1    Sep. 17, 2015

(30) Foreign Application Priority Data
Oct. 24, 2012   (IT) .............................. UD2012A0179

(51) Int. Cl.
*A61F 2/34* (2006.01)
*A61F 2/30* (2006.01)

(52) U.S. Cl.
CPC ............ *A61F 2/34* (2013.01); *A61F 2/30771* (2013.01); *A61F 2002/30332* (2013.01);
(Continued)

(58) Field of Classification Search
CPC .. A61F 2/34; A61F 2/30771; A61F 2002/348; A61F 2002/30332;
(Continued)

(56) References Cited

U.S. PATENT DOCUMENTS 5,310,408 A * 5/1994 Schryver ............ A61B 17/8605
623/22.11
5,405,392 A * 4/1995 Deckner .................. A61F 2/34
623/22.24
(Continued)

FOREIGN PATENT DOCUMENTS

DE    196 16 059 A1    10/1997
DE    197 01 536 A1    2/1998
(Continued)

OTHER PUBLICATIONS

International Search Report and Written Opinion for PCT/IB2013/002378, dated Mar. 25, 2014.

*Primary Examiner* — Alvin Stewart
(74) *Attorney, Agent, or Firm* — Marshall, Gerstein & Borun LLP

(57) ABSTRACT

Acetabular prosthesis comprising an acetabular cup, defining a coupling cavity, and an insert, able to be inserted inside the coupling cavity. The acetabular cup and the insert have a common coupling axis and comprise respective clamping means for their reciprocal clamping in an assembled condition.

20 Claims, 6 Drawing Sheets

(52) U.S. Cl.
CPC ........... *A61F 2002/30484* (2013.01); *A61F 2002/30505* (2013.01); *A61F 2002/30838* (2013.01); *A61F 2002/3403* (2013.01); *A61F 2002/348* (2013.01); *A61F 2002/3411* (2013.01); *A61F 2002/3414* (2013.01); *A61F 2240/001* (2013.01); *Y10T 29/49959* (2015.01)

(58) Field of Classification Search
CPC .... A61F 2002/30484; A61F 2002/3403; A61F 2002/3408
See application file for complete search history.

(56) References Cited

U.S. PATENT DOCUMENTS

| | | | | |
|---|---|---|---|---|
| 5,480,448 | A * | 1/1996 | Mikhail | A61F 2/34 623/22.24 |
| 5,571,201 | A * | 11/1996 | Averill | A61F 2/34 606/86 R |
| 6,610,097 | B2 * | 8/2003 | Serbousek | A61F 2/34 623/22.24 |
| 6,682,567 | B1 * | 1/2004 | Schroeder | A61B 17/1666 606/91 |
| 6,916,342 | B2 * | 7/2005 | Frederick | A61F 2/32 623/22.2 |
| 8,123,815 | B2 * | 2/2012 | Meridew | A61F 2/34 623/22.29 |
| 8,382,850 | B2 * | 2/2013 | Dalla Pria | A61F 2/34 623/22.21 |
| 8,556,981 | B2 * | 10/2013 | Jones | A61F 2/30907 623/18.11 |
| 8,771,367 | B2 * | 7/2014 | Armacost | A61F 2/34 623/22.24 |
| 2002/0040245 | A1 * | 4/2002 | Lester | A61B 17/1666 623/22.23 |
| 2003/0050705 | A1 * | 3/2003 | Cueille | A61F 2/30767 623/22.24 |
| 2003/0105529 | A1 * | 6/2003 | Synder | A61F 2/34 623/22.24 |
| 2003/0153982 | A1 * | 8/2003 | Pria | A61F 2/34 623/22.24 |
| 2006/0167556 | A1 * | 7/2006 | Lazennec | A61F 2/34 623/22.24 |
| 2006/0190089 | A1 * | 8/2006 | Montoya | A61F 2/34 623/22.28 |
| 2009/0287312 | A1 * | 11/2009 | Berger | A61F 2/30721 623/22.29 |
| 2010/0191345 | A1 * | 7/2010 | Pressacco | A61L 27/047 623/22.26 |
| 2011/0009975 | A1 * | 1/2011 | Allen | A61F 2/32 623/22.24 |
| 2011/0015753 | A1 * | 1/2011 | Meridew | A61F 2/34 623/22.24 |
| 2011/0087335 | A1 * | 4/2011 | Newsome | A61F 2/30721 623/22.29 |
| 2011/0282460 | A1 * | 11/2011 | Holtmann | A61F 2/34 623/22.24 |
| 2012/0095569 | A1 | 4/2012 | Kellar et al. | |
| 2012/0143343 | A1 * | 6/2012 | Meridew | A61F 2/34 623/22.15 |
| 2012/0185059 | A1 * | 7/2012 | Vankoski | A61F 2/4684 623/22.24 |
| 2013/0268083 | A1 * | 10/2013 | McMinn | A61F 2/30771 623/22.24 |
| 2014/0343682 | A1 * | 11/2014 | Mangan | A61F 2/34 623/22.24 |

FOREIGN PATENT DOCUMENTS

| | | |
|---|---|---|
| EP | 1 712 206 A2 | 10/2006 |
| WO | WO-2004/017870 A1 | 3/2004 |
| WO | WO-2006/125711 A1 | 11/2006 |
| WO | WO-2008/146141 A2 | 12/2008 |

* cited by examiner

ACETABULAR PROSTHESIS AND CORRESPONDING METHOD FOR PRODUCTION AND ASSEMBLY

FIELD OF THE INVENTION

The present invention concerns an acetabular prosthesis associable to a natural acetabular seating of the hip to function as the positioning and rotation seating for the head of a femoral prosthesis.

The present invention also concerns the method to produce and assemble the acetabular prosthesis.

BACKGROUND OF THE INVENTION

In the field of orthopedic hip prostheses, it is known to produce acetabular prostheses consisting of an insert with a semispherical cavity which acts as a positioning and rotation seating for the head of the femoral prosthesis.

The insert, in its turn, is normally disposed inside a mating shell, or acetabular cup, with an internal cavity, made of osteo-compatible metal material, for example with a titanium base or a cobalt base, attached in an acetabular seating of the hip.

In this context, resurfacing prostheses are known, suitable to be attached on the head of the femur, leaving it substantially intact.

Resurfacing systems have been used for many years in reconstruction surgery of the hip with the purpose of:

preserving the neck and a portion of the head of the femur in active, young patients;
  using diameters of the head which are nearer to the anatomical diameter, compared with traditional implants, in order to restore the articular biomechanics and at the same time to guarantee a smaller risk of dislocation;
  facilitating possible future revisions with a traditional implant, since the proximal part of the femur is intact, instead of with revision implants.

The resurfacing systems on the market traditionally provide couplings of the metal-metal type.

Recently, some resurfacing systems have shown a higher failure rate than that of traditional implants. More generally, a possible drawback has emerged in the case of metal-metal couplings, due to the release of metal ions, which have developed following wear on the components in the human body. These ions have different side effects including deterioration in the tissues surrounding the implant, loss of the implant itself and in some cases effects at a systemic level (heart, nervous system, etc. . . . ). The development of these wear phenomena is more evident in cases where the acetabular implant is not perfectly positioned in terms of inclination and turning. Consequently, even though, by using metal-metal couplings, very limited thicknesses are obtained which adapt well to the production of resurfacing prostheses, it is better to avoid this type of coupling because of the drawbacks described above.

From the document DE-A-19616059 it is known to make a prosthesis which has a cylindrical coupling, in particular, which provides the possibility of an insert with a diameter larger than that of the cup. This technique is usually used in cylindrical forced couplings in mechanics. More specifically, the coupling provided achieves a congruency between the two spherical surfaces, in order to have a better distribution of the contact.

Document DE-A-19701536 describes an articulation prosthesis of the known type, which provides a conical coupling of inserts made of ceramic, but without providing a mechanical forcing in proximity to the coupling plane between acetabular cup and insert defined along the coupling axis.

Document EP-A-1.712.206 describes an acetabular prosthesis which provides a conical coupling similar to DE-A-19701536.

Document WO-A-2004/017870 describes an expandable cotyloid cavity, or acetabular cup, which is made elastic by means of radial sections and which provides a throat inside which a flange or tooth of the insert is coupled in snap-in manner, in order to prevent it from coming out. In substance, the coupling occurs by connecting the tooth into the throat and subsequent conical coupling.

Document WO-A-2006/125711 describes a prosthesis provided with recesses made only directly under the surface, which connect with the outside through transverse apertures.

Document US-A-2012/095569 describes a prosthetic joint which comprises a contact member made of metal or ceramic with an osteo-integrating resurfacing surface, such as trabecular metal, texturized metal, sintered or extruded integration textures, which is made only on the surface, not wholly throughout the component without a break in continuity.

One purpose of the present invention is therefore to produce an acetabular prosthesis which on the one hand can be made with reduced thicknesses and on the other hand is compatible and has good mechanical resistance, in particular to wear, and thus prevents the release of ions.

Another purpose of the present invention is to produce an acetabular prosthesis of a total prosthesis of the hip which can be configured as a resurfacing prosthesis, thus obtaining the typical advantages of this type of prosthesis, but without the drawbacks of the metal-metal coupling described above.

Another purpose of the present invention is to produce an acetabular prosthesis of a total prosthesis of the hip, the insert of which, once disposed inside the acetabular cup or shell, maintains, during normal use, the position determined during the operation of inserting the acetabular cup inside the acetabular seating and of the prosthesis of the femoral head, inside the insert, preventing rotation with respect to the common axis of symmetry.

Another purpose of the present invention is to perfect a production method which optimizes the assembly and installation of the acetabular prosthesis.

The Applicant has devised, tested and embodied the present invention to overcome the shortcomings of the state of the art and to obtain these and other purposes and advantages.

SUMMARY OF THE INVENTION

The present invention is set forth and characterized in the independent claims, while the dependent claims describe other characteristics of the invention or variants to the main inventive idea.

In accordance with the above purposes, an acetabular prosthesis according to the present invention, which overcomes the limits of the state of the art and eliminates the defects therein, is insertable inside a natural acetabular seating of the hip to act as a positioning and rotation seating for the head of a femoral prosthesis.

The acetabular prosthesis comprises an acetabular cup, in turn comprising an internal surface defining a coupling cavity, and an insert able to be inserted inside the coupling cavity and in turn comprising an external surface.

The acetabular cup and the insert have a common coupling axis and comprise corresponding clamping means for their reciprocal clamping in an assembled condition.

According to the present invention, in a disassembled condition the coupling cavity of the acetabular cup has an internal diameter which is less than the largest external diameter of the insert; moreover, in the assembled condition the largest external diameter of the insert is equal to the internal diameter of the coupling cavity of the acetabular cup. In some forms of embodiment, the internal diameter of the coupling cavity of the acetabular cup is considered in correspondence to a coupling plane between the acetabular cup and the insert, defined along the coupling axis.

According to some forms of embodiment of the present invention, the clamping means comprise a first clamping surface, made on the internal surface of the acetabular cup, and a second clamping surface, made on the external surface of the insert and cooperating with the first clamping surface.

The first and the second clamping surface have a truncated cone shape with a different inclination between them with respect to the coupling axis.

According to one form of embodiment of the invention, a conical coupling is made between the insert and the acetabular cup, with an imposed interference, variable along the axis of symmetry.

In particular, unlike in the state of the art, the insert can be coupled to the acetabular cup by means of forced conical coupling.

Indeed the present invention achieves a conical coupling with forcing of the insert and the acetabular cup, in particular obtaining said forcing in proximity to the coupling plane defined above.

According to another possible feature of the present invention, the variable interference during use is maximum in proximity to the maximum diameters of the cones and minimum in proximity to the minimum diameters of the cones defining the first and the second clamping surfaces.

The variable interference is able to compensate the deformations that the insert undergoes during the assembly steps of the acetabular prosthesis.

In this way, we maintain that the present invention is suitable to preserve the advantages deriving from the production of resurfacing prostheses, but also provides greater primary stability to the prosthesis itself.

In variant embodiments, the first clamping surface has a smaller inclination compared to the inclination of the second clamping surface.

According to another feature of the present invention, at least one of either the acetabular cup or the insert is made of ceramic material.

In example embodiments, the insert is made of ceramic material.

The choice of ceramic material allows to adopt relatively thin thicknesses and, at the same time, to obtain optimum mechanical and anti-wear characteristics, preventing the release of metal ions. Ceramic material is also bio-compatible.

Ceramic-ceramic couplings have a reduced rate of wear, they do not release metal ions and they are less sensitive to the positioning of the implant compared with metal-metal systems. In particular, with the present invention it is possible to obtain reduced thicknesses of the acetabular prosthesis, to maintain the necessary mechanical properties, and, what is more, to prevent the problem of wear and release of ions.

According to another feature of the present invention, the acetabular cup is shaped so as to comprise a through aperture, in correspondence to its polar region.

According to another feature of the present invention, the insert is shaped so as to comprise, in a polar region thereof, a centering element able to be inserted inside the through aperture.

The centering element and the through aperture are able to allow the centering of the acetabular cup and the insert during the assembly step.

The present invention also concerns a method to assemble an acetabular prosthesis as described above, such assembly being typically carried out during an industrial production step.

The method provides:
  to make available an acetabular cup comprising an internal surface defining a coupling cavity,
  to make available an insert able to be inserted inside the coupling cavity and comprising an external surface,
  to couple the acetabular cup and the insert along a common coupling axis and to clamp them reciprocally in an assembled condition using respective clamping means.

According to the present invention, before coupling, in a disassembled condition, the coupling cavity of the acetabular cup has an internal diameter which is less than the largest external diameter of the insert while, after the coupling, in the assembled condition, the internal diameter of the coupling cavity of the acetabular cup is equal to the largest external diameter of the insert.

In some forms of embodiment, the internal diameter of the coupling cavity of the acetabular cup is considered in correspondence to a coupling plane between the acetabular cup and the insert defined along the coupling axis.

Moreover, in some forms of embodiment, the clamping of the acetabular cup and the insert is achieved by means of clamping means which comprise:
  a first clamping surface, made on the internal surface of the acetabular cup,
  a second clamping surface, made on the external surface of the insert, and cooperating with the first clamping surface.

The first clamping surface and the second clamping surface are a truncated cone shape, with an inclination different from each other with respect to the coupling axis, so as to obtain a conical coupling of the insert and the acetabular cup, with variable interference, along the coupling axis.

In some forms of embodiment, the method to assemble the acetabular prosthesis comprises at least a step in which the acetabular cup is gripped by elastic gripping means in correspondence to a through aperture, a step in which the insert is positioned on a support and centering element, a step in which the elastic gripping means are moved and the acetabular cup is coupled, by variable interference, with the insert, making the first clamping surface and the second clamping surface cooperate with each other, and a step in which the elastic gripping means release the acetabular cup coupled with the insert.

In some forms of embodiment, the method includes a preliminary step of aligning and centering the elastic gripping means and the insert, positioned on the support and centering element, moving the elastic gripping means downward.

In some forms of embodiment, after the alignment and centering of the elastic gripping means and the insert, the elastic gripping means are raised, the insert is removed from the support and centering element, the acetabular cup is placed on the support and centering element, the elastic gripping means are moved downward to grip the acetabular cup, the elastic gripping means associated to the acetabular cup are raised and the insert is once again positioned on the support and centering element in order to proceed with the conical coupling.

In some variants, the assembly can be obtained by applying a thermal load, or a thermal deformation.

In other variants, the assembly can be obtained mechanically, or by means of mechanical forcing.

Other variants can provide an assembly made by combining the application of a thermal load to a mechanical assembly.

BRIEF DESCRIPTION OF THE DRAWINGS

These and other characteristics of the present invention will become apparent from the following description of some forms of embodiment, given as a non-restrictive example with reference to the attached drawings wherein.

DETAILED DESCRIPTION OF SOME FORMS OF EMBODIMENT

We shall now refer in detail to the various forms of embodiment of the present invention, of which one or more examples are shown in the attached drawing. Each example is supplied by way of illustration of the invention and shall not be understood as a limitation thereof. For example, the characteristics shown or described insomuch as they are part of one form of embodiment can be adopted on, or in association with, other forms of embodiment to produce another form of embodiment. It is understood that the present invention shall include all such modifications and variants.

Figure 1:
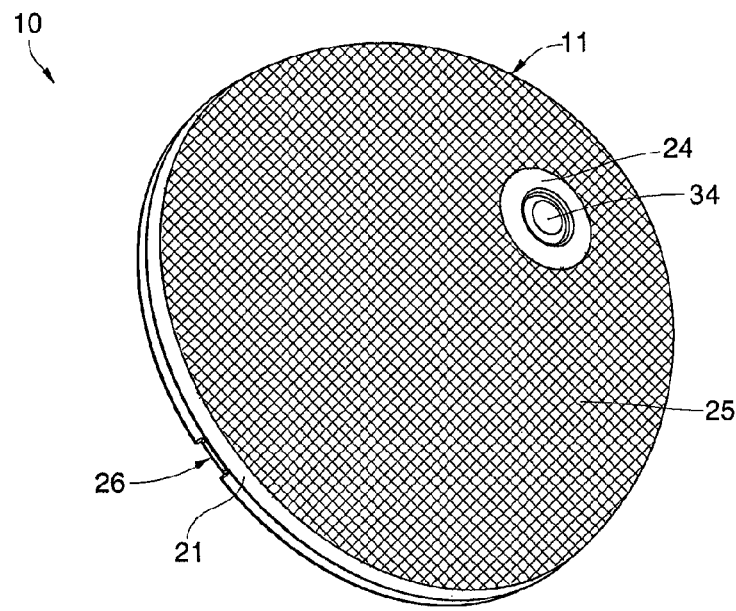
FIG. 1 is a perspective view of an acetabular prosthesis according to some forms of embodiment of the present invention.
Figure 2:
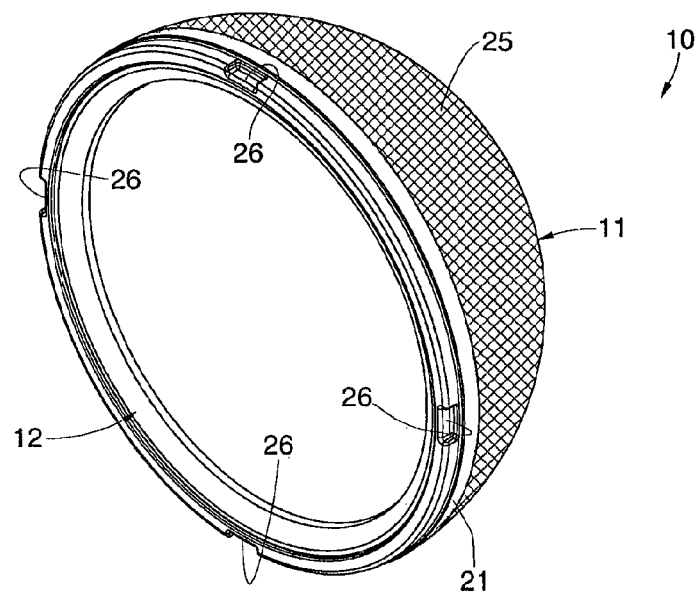
FIG. 2 is another perspective view of the acetabular prosthesis in FIG. 1.

With reference to FIGS. 1 and 2, an acetabular prosthesis 10 according to the present invention is able to be inserted inside an acetabular seating, not shown in the drawings, of the hipbone of a patient, acting as a positioning and rotation seating for the head of a femoral prosthesis, also not shown in the drawings. In non-restrictive example embodiments of the present invention, we maintain that the acetabular prosthesis 10 can be applied effectively to achieve resurfacing prostheses.

Figure 3:
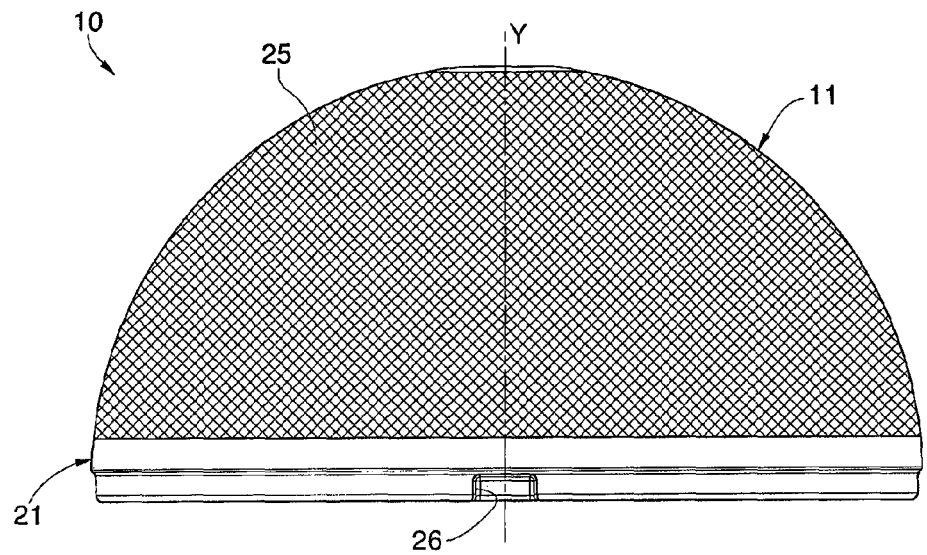
FIG. 3 is a lateral view of the acetabular prosthesis in FIG. 1.

In some forms of embodiment, the acetabular prosthesis 10 can substantially be shaped like a hemi-spherical or semi-spherical cap, which is hollow inside and, in this case shown by way of example, axial symmetric with respect to an axis of symmetry Y (FIGS. 3 and 4), also called coupling axis.

According to the present invention, the acetabular prosthesis 10 mainly comprises two elements, that is, an acetabular cup 11 and a mating insert 12, both of a substantially semi-spherical shape which are reciprocally constrained and assembled by conical coupling with interference that is variable and imposed along a common coupling axis which in this case is represented by said axis Y.

In particular, in some forms of embodiment, the acetabular cup or shell 11 is insertable inside the acetabular seating of the hip, and the mating insert 12 is insertable inside the acetabular cup 11.

The configuration of the acetabular prosthesis 10 defines overall a semi-spherical cavity 13.

The acetabular cup 11 can in this case be made of titanium, titanium alloys, or in any case a material with a titanium base.

Figure 5:
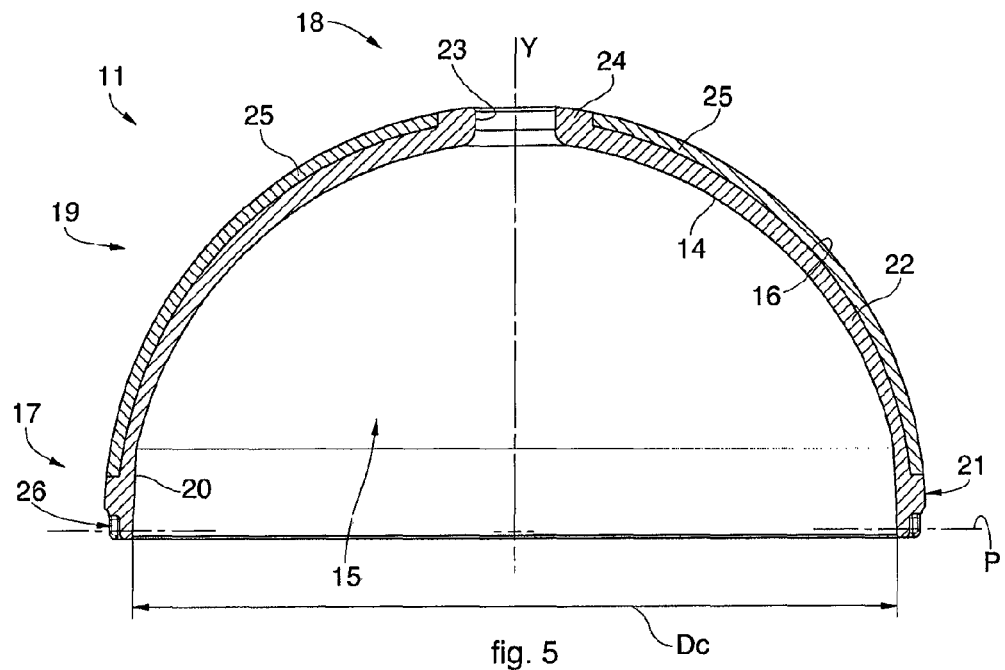
FIG. 5 is a part of FIG. 4.

The acetabular cup 11 can comprise an internal surface 14 (FIG. 5), which can define a coupling cavity 15, in this case semi-spherical, and an external surface 16 which, during use, faces toward the bone of the acetabular seating. The acetabular cup 11 can comprise or be defined by an equatorial band 17, a polar region 18 and an intermediate zone 19, the latter provided between the equatorial band 17 and the polar region 18, with a greater extension and of a semi-spherical shape.

Figure 7:
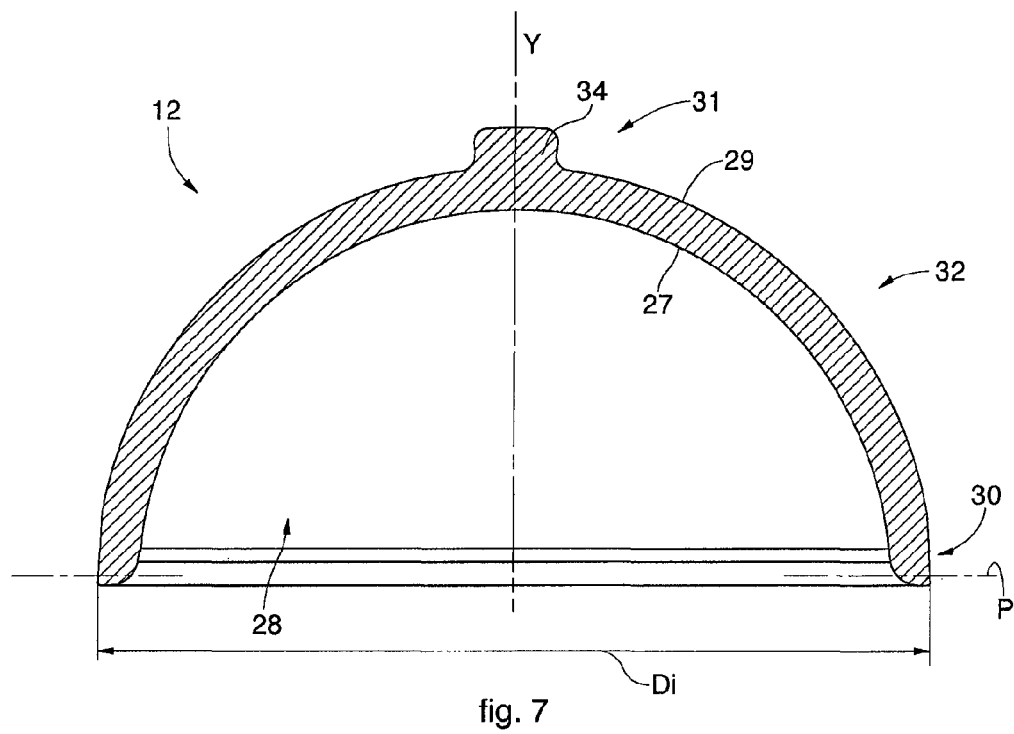
FIG. 7 is another part of FIG. 4.

According to some forms of embodiment of the present invention, in a disassembled condition the coupling cavity 15 of the acetabular cup 11 has an internal diameter Dc (FIG. 5) which is less than a largest external diameter Di (FIG. 7) of the insert 12.

Figure 4:
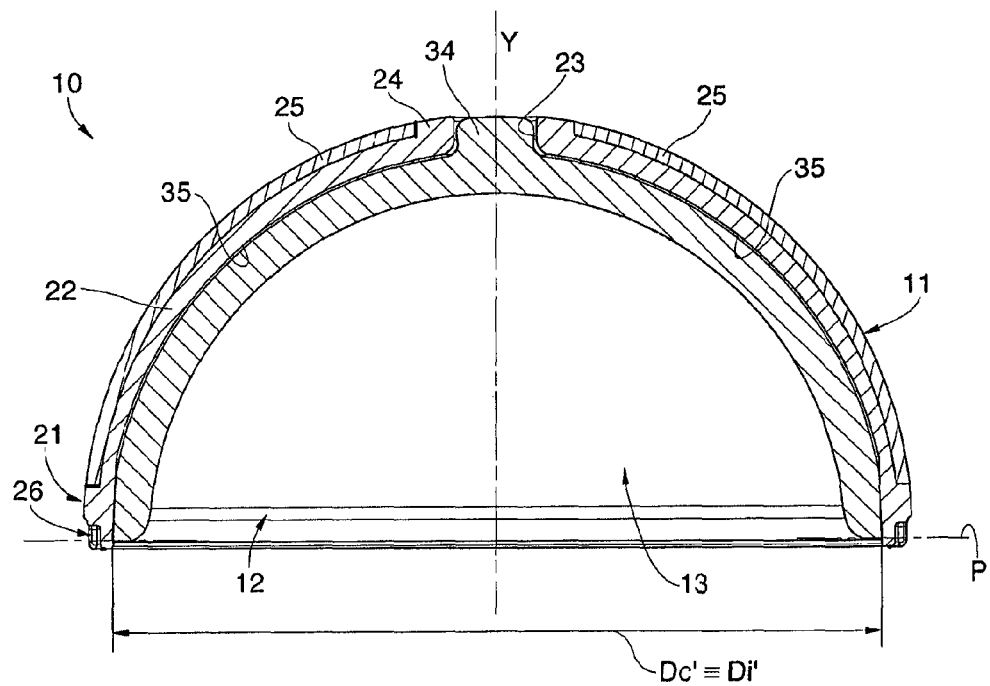
FIG. 4 is a transverse section of the acetabular prosthesis in FIG. 3.

Moreover, according to the present invention, in the assembled condition the largest external diameter, indicated by Di' in FIG. 4, of the insert 12 is equal, following mechanical and/or thermal deformation, to the internal diameter, indicated by Dc' in FIG. 4, of the coupling cavity 15 of the acetabular cup 11.

In particular, in some forms of embodiment of the invention, an interference "i" can be identified given by the difference between the values of the diameters Di and Dc, external and internal, respectively of the insert 12 and the acetabular cup 11, in the disassembled condition:

$$i = Di - Dc$$

Without being constrained by theory, in practice we maintain that the stable coupling of insert 12 and acetabular cup 11 is given in large part by the deformation of the material of the acetabular cup 11 which, following the forced coupling, mechanical and/or thermal, with the insert 12, has a deformation which increases the internal diameter from Dc to Dc'.

In possible forms of embodiment, values "i" of diameter interference can be equal to or more than 0.01 mm, for example can vary in a range between 0.01 and 0.25 mm, and can include every possible sub-range. Examples of embodiments of lower limits of diametral interference values "i" can be 0.01 mm, 0.0125 mm, or 0.025 mm, or 0.05 mm. Examples of embodiments of higher limits of diametral interference values "i", which can be combined with examples of embodiment cited of lower limits of diametral interference values "i", can be 0.25 mm, or 0.20 mm, or again 0.15 mm. For example, a sub-range of diametral interference values "i" can be between 0.025 mm and 0.20 mm, or another example of sub-range of diametral interference values "i" can be between 0.05 mm and 0.15 mm.

For the sake of completeness, we maintain that the shape or size of the insert 12 can also be minimally deformed, and that as a consequence the external diameter of the insert 12 varies slightly from Di to the value Di' after coupling with the acetabular cup 11. However, we maintain that in most cases the difference in absolute value between Di and Di' is negligible, in that the deformation of the material which constitutes the insert 12 is negligible, while the difference between Dc and Dc' is significant. Indeed, as we said, the largest deformation occurs on the acetabular cup 11, the internal diameter of which increases from Dc to Dc'.

In some forms of embodiment, the internal diameter Dc, Dc' of the coupling cavity 15 of the acetabular cup 11 is considered, both in the disassembled condition and in the assembled condition, in correspondence to a coupling plane P of the acetabular cup 11 and the insert 12, defined along the coupling axis Y.

Figure 6:
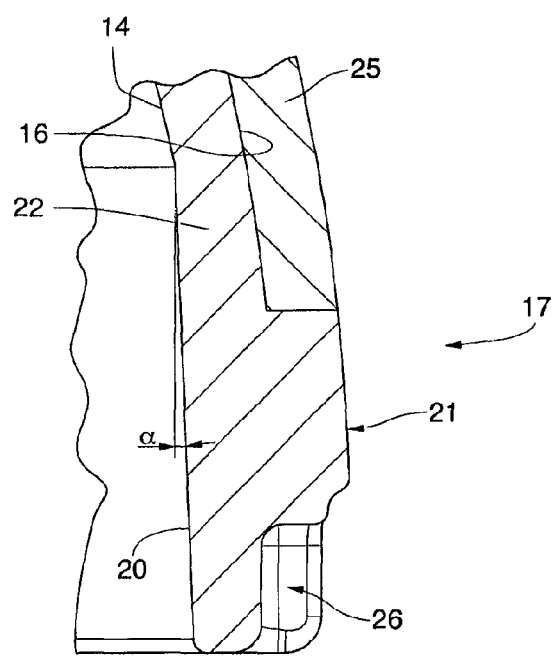
FIG. 6 is an enlarged detail of FIG. 5.

In some forms of embodiment, in correspondence to the equatorial band 17, the internal surface 14 can be shaped so as to comprise a first clamping surface 20, shaped like a truncated cone, with an inclination α with respect to the axis Y (FIG. 6) and able to achieve the reciprocal clamping with the insert 12, as will be seen hereafter in the present description. Moreover, the equatorial band 17 can be shaped so as to comprise an external ring 21. In some forms of embodiment, the external ring 21 is a solid and compact part of the acetabular cup 11.

The external ring 21 can have the function of modulating the rigidity of the whole acetabular cup 11. By way of example, we maintain that the greater the height of the external ring 21, the greater is the overall rigidity of the acetabular cup 11. In some forms of embodiment, the desired rigidity can be obtained, in the design stage, according to the sizes of the prosthesis to be made, by varying the height of the external ring 21. The polar region 18 can be shaped so as to have a through aperture 23 of a circular shape, delimited by an upper ring 24, configured for example as a protruding annular projection.

In some forms of embodiment, the acetabular cup 11 can comprise, in the space between the external ring 21 and the upper ring 24 of the equatorial band 17, a solid and compact internal part 22 and a trabecular part, or reticular trabecular structure 25, in this case external, associated to the external surface 16. The trabecular part 25 can be defined by a lattice which, for example, acts as a gripping and osseo-integration element for the hipbone during the re-growth step following the operation undergone by the patient.

In other forms of embodiment, the trabecular part 25 can be in a single body with the solid and compact internal part 22 and with the external ring 21, that is, from the inside to the outside, the material which constitutes the acetabular cup 11 is solid, in correspondence to the external ring 21 and, continuous with the material, varies in order to subsequently define the structure of the trabecular part 25.

In other forms of embodiment, the acetabular cup 11 can consist completely of the trabecular part 25.

In some forms of embodiment, the structure of the trabecular part 25 can be a lattice of cells, achieving a plurality of three-dimensional cavities disposed, open and intercommunicating, connected with each other. The lattice can be solid with the solid and compact internal part 22 and with the external ring 21. In some forms of embodiment, at least part of the lattice of the trabecular part 25 can be formed, without any break in continuity, by one or more models of a plurality of geometric meshes which are repeated in space on all the trabecular part 25, having a cellular geometry with open and contiguous elementary cells, so as to define a plurality of polygons, such as hexagons, with non-coplanar vertexes, with a spatial development delimiting the cavities, so that the lattice is able to promote osseo-integration.

In some forms of embodiment, the structure of the trabecular part 25 mentioned above, possibly in continuity with the solid and compact internal part 22, can be obtained using techniques such as Electron Beam Melting (EBM), or Selective Laser Melting (SLM). Example embodiments are described in the international application WO-A-2008/146141 in the name of the Applicant.

In some forms of embodiment, the acetabular cup 11 can also comprise a plurality, in this case for example four, niches 26 on the external surface 16 of the equatorial band 17, to facilitate the orientation and positioning of the acetabular cup 11 in the acetabular seating.

The insert 12, in this case made of ceramic material, can comprise an internal surface 27 (FIG. 7), which can define a semi-spherical cavity 28, and an external surface 29, which during use faces toward the internal surface 14 of the acetabular cup 11. In this case too, the insert 12 can for example be defined by an equatorial band 30, a polar region 31 and an intermediate zone 32.

The insert 12 made of ceramic material allows to adopt relatively thin thicknesses and, at the same time, to obtain optimum mechanical characteristics, resistance to wear, biocompatibility and to prevent the risk of metal ions.

Figure 8:
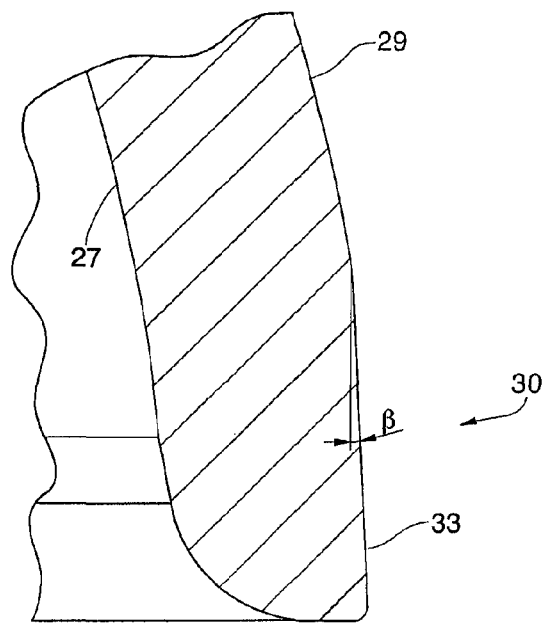
FIG. 8 is an enlarged detail of FIG. 7.

The external surface 29, in correspondence to the equatorial band 30, can be shaped so as to comprise a second clamping surface 33, shaped like a truncated cone and with an inclination β (FIG. 8) greater than the inclination α of the first clamping surface 20 of the acetabular cup 11.

Consequently, according to some forms of embodiment of the present invention, the first clamping surface 20 and the second clamping surface 33 can be truncated cone shaped with an inclination α, β different from each other with respect to the coupling axis Y, so as to achieve a coupling of the insert 12 and the acetabular cup 11 with interference "i" that varies along the axis of symmetry Y.

In substance, some forms of embodiment define that said largest external diameter Di, Di' of the insert 12 is the largest base diameter of the truncated cone shape of the second clamping surface 33.

Therefore, some forms of embodiment define that said largest internal diameter Dc, Dc' of the acetabular cup 11 is the diameter of the truncated cone shape of the first clamping surface 20 in correspondence to the annular band of cooperation and coupling with the second clamping surface 33 of the insert 12, along the coupling plane P.

Having already defined above the interference "i" as the difference between the diameters Di and DC, it is clear that this size refers to the base diameters of the truncated cones of the clamping surfaces 20 and 33. With reference to the interference "i", in FIG. 11 its variability is schematically shown, in particular decreasing along the coupling axis Y going from the outside to the inside, where it has a maximum value ($i_{max}$) in correspondence to the largest diameters Dc, Di, internal and external respectively, in the disassembled condition of the acetabular cup 11 and of the insert 12, and a minimum value ($i_{min}$), equal to zero, where the two diameters Dc, Di, varying in height along the coupling axis Y, would assume the same value. In this case, said coupling plane P can therefore be defined as the through plane for the annular region of contact and coupling of acetabular cup 11 and insert 12 in the assembled condition, in correspondence to the position for which the interference "i" assumes the value ($i_{max}$) which there would be in the disassembled condition.

In some forms of embodiment, the insert 12 can be shaped so as to comprise, in the polar region 31, a centering peg 34 able to be inserted inside the through aperture 23, with a diameter a little less than that of the through aperture 23.

Figure 9:
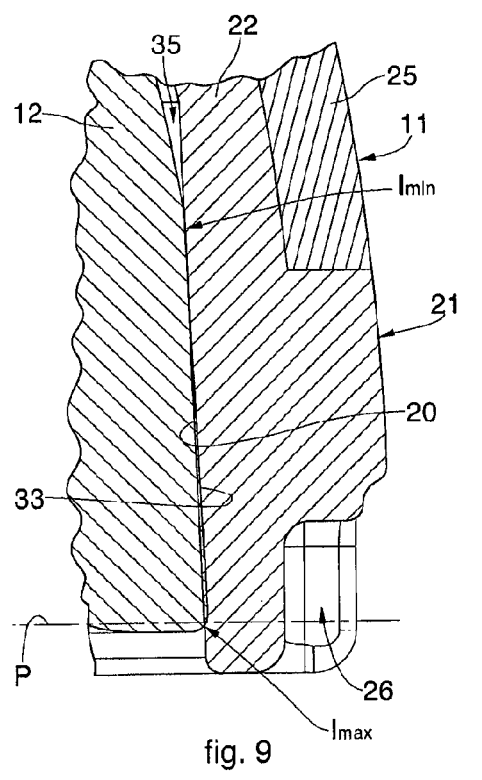
FIG. 9 is an enlarged detail of FIG. 4.
Figure 11:
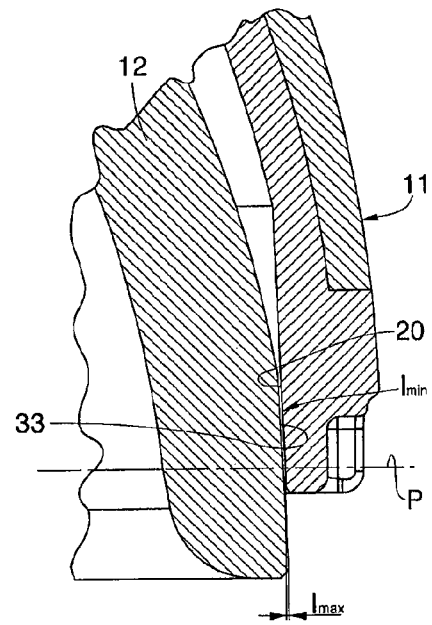
FIG. 11 is a schematic representation of a part of the present invention.

As we said above, the two different inclination values, that is, conicity, α and β of the clamping surfaces 20 and 33 with respect to the axis Y, ensure that the coupling of the insert 12 and the acetabular cup 11 occurs by interference "i" (FIG. 9). In particular, we have maximum variable interference "i" on the maximum diameter of the cone, and minimum, in this case zero, on the minimum diameter of the cone (FIGS. 9 and 11). This configuration is able to compensate the deformations in the monitoring step and to guarantee a solid coupling.

Moreover, the presence of the centering peg 34 can facilitate, in the assembly step, the centering of the insert 12 with respect to the acetabular cup 11.

Figure 10:
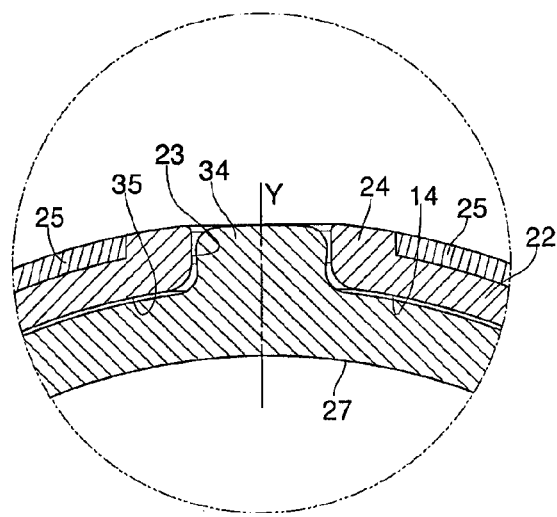
FIG. 10 is another enlarged detail of FIG. 4.

The acetabular cup 11 and the insert 12 can be configured so as to cooperate with each other, during assembly, only using the clamping surfaces 20 and 33, defining an interspace 35 in correspondence to the intermediate zones 19 and 32 and the polar regions 18 and 31 (FIG. 10). The interspace 35, during assembly, has the function of ensuring that the constraint is caused by the conical coupling. During normal use the insert 12 and the acetabular cup 11 can cooperate in contact with each other.

The acetabular prosthesis 10, in its entirety, confers an optimum stability to the insert 12 and the acetabular cup 11, both in the insertion step of the acetabular prosthesis 10 into the acetabular seating, and also in the insertion step of the head of the femoral prosthesis, or the natural femoral head, inside the insert 12.

According to some forms of embodiment, the coupling of the acetabular cup 11 and the insert 12 can occur as described hereinafter in relation to the schematic representation in FIG. 12, which respectively show two variants of possible assembly.

For the assembly, the present invention can use elastic gripping means driven by a press 42 configured to apply a desired vertical thrust. In variant embodiments, the elastic gripping means are for example elastic grippers 37 vertically mobile by means of the press 42. The elastic grippers 37 are equipped with an elastic thruster 38 with a piston which has elastic gripping ends 39 of the flexible type able to deform elastically during opening and closing. The elastic gripping ends 39 protrude from an abutment surface 46 of the elastic thruster 38 of a curvilinear shape, mating with a contact portion 47 of the polar region of the acetabular cup 11 which surrounds the through aperture 23.

The elastic grippers 37 can comprise a containing chamber 43 for the travel of the elastic thruster 38, in which elastic cushioning means are provided, such as a spring 44 for example. The elastic thruster 38 can normally be in an inactive position on the bottom of the containing chamber 43, as can be seen in FIG. 12, step A.

Figure 12:
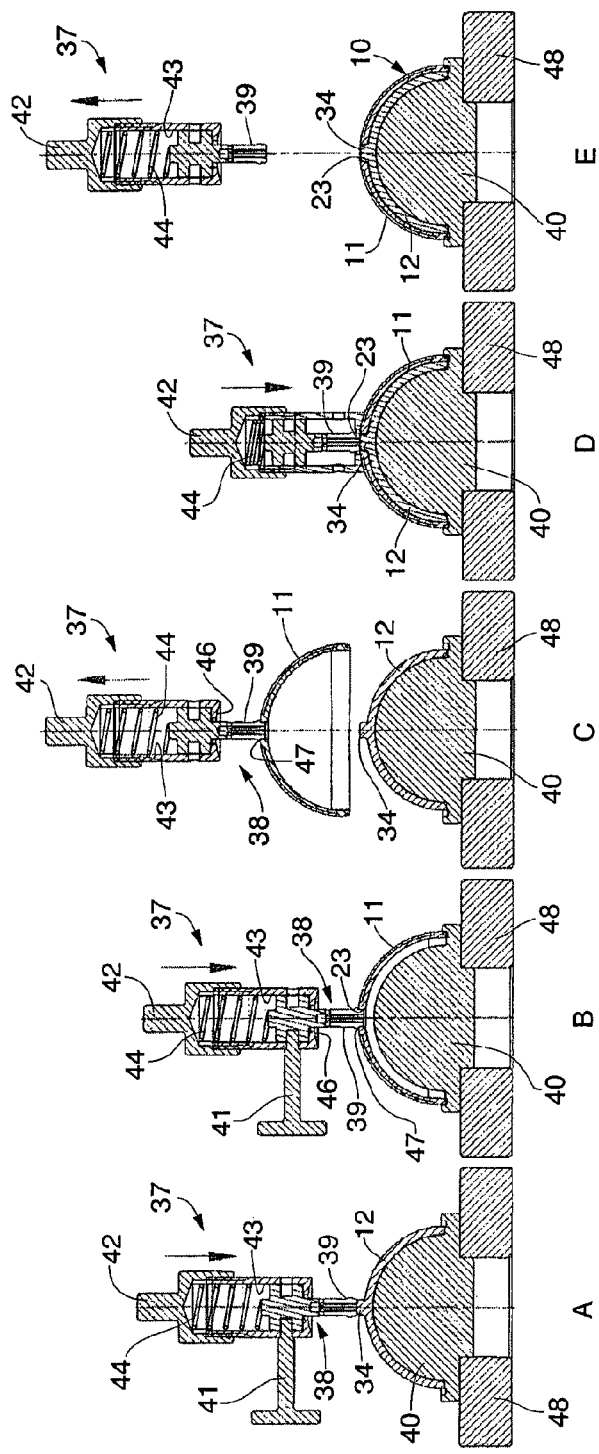
FIG. 12 schematically shows a variant of the method to assemble the acetabular prosthesis in FIG. 1.

In some forms of embodiment, the assembly method, typically carried out during the industrial production step, can include a preliminary step of centering and aligning the insert 12 and the elastic grippers 37 (FIG. 12 step A). The insert 12 can be positioned on a support and centering element 40 disposed, in its turn, on a support block 48. The support and centering element 40 has the profile, in negative, of the internal surface 27 of the insert 12. The centering is carried out by moving the elastic grippers 37 downward and aligning them to the centering peg 34, until they contact the latter. In this case, a clamping element 41 is provided which cooperates with the elastic thruster 38, clamping its travel, to prevent the elastic thruster 38 from returning upward (FIG. 12, step A).

Subsequently, it is necessary to mount the acetabular cup 11 on the elastic grippers 37. To do this, as seen in FIG. 12, the elastic grippers 37, once aligned to the insert 12, are raised and the insert 12 is removed from the support and centering element 40.

The acetabular cup 11 is then positioned on the latter and the elastic grippers 37 are again lowered, keeping the clamping element 41 inserted, until the cooperation is determined between the elastic gripping end 39 and the through aperture 23 of the acetabular cup 11 (FIG. 12 step B). We maintain that the removal of the insert 12 from the support and centering element 40 facilitates the mounting of the acetabular cup 11 onto the elastic grippers 37, since otherwise the through aperture 23 would be occupied by the centering peg 34 and could not be engaged by the elastic gripping ends 39.

Subsequently, the elastic grippers 37, and the acetabular cup 11 solid with it, are again raised, in order to place the insert 12 once again on the support and centering element 40 (FIG. 12, step C). The clamping element 41 can be removed in order to allow the travel of the elastic thruster 38 as explained below.

Then, the elastic grippers 37 are once again moved downward and the acetabular cup 11 is placed on the insert 12, applying a suitable thrust using the press 42, making the first clamping surface 20 and the second clamping surface 33 cooperate with each other, so as to obtain the conical coupling by variable interference as described above (FIG. 12 step D): The cooperation between the first clamping surface 20 and the second clamping surface 33 begins when the abutment surface 46 of the elastic thruster 38 contacts the contact portion 47 of the polar region 18 of the acetabular cup 11. In fact, at this point, the travel of the elastic thruster 38 is caused, backward with respect to its inactive position on the bottom of the containing chamber 43, until the elastic gripping ends 39 are positioned in the containing chamber 43, disengaging the through aperture 23 (FIG. 12, step D). This movement is elastically controlled and cushioned by the spring 44, which as a consequence is progressively compressed (FIG. 12, step D). The elastic thruster 38 retracts until the elastic gripping ends 39 are uncoupled from the through aperture 23, also following the insertion of the centering peg 34. In this way, moreover, the through aperture 23 is positioned around the centering peg 34, ensuring the centering of the acetabular cup 11 on the insert 12 (FIG. 12, step D).

In some forms of embodiment, in step D the assembly of the acetabular cup 11 and insert 12 can be obtained only mechanically, by means of said conical coupling, or by applying a thermal load, so that the thermal dilation of the material of the acetabular cup 11 due to heating facilitates the conical coupling of the acetabular cup 11 and insert 12, or by means of a combination of these techniques.

In any case, the technique selected is suitable to obtain the forced coupling of the insert 12, which in the disassembled condition has a largest external diameter Di larger than the internal diameter Dc of the acetabular cup 11, so that, in the assembled condition, the largest external diameter Di' is equal to the internal diameter Dc' of the acetabular cup 11.

Subsequently, the elastic grippers 37 are raised, separating from the acetabular cup 11 which stays coupled to the insert 12 by variable interference (FIG. 12, step E). As it rises, the elastic thruster 38 is once again thrust toward the outside by the extension of the spring 44 (FIG. 12, step E).

It is clear that modifications and/or additions of parts may be made to the acetabular prosthesis and the corresponding method as described heretofore, without departing from the field and scope of the present invention.

It is also clear that, although the present invention has been described with reference to a specific example, a person of skill in the art shall certainly be able to achieve many other equivalent forms of acetabular prosthesis and corresponding method, having the characteristics as set forth in the claims and hence all coming within the field of protection defined thereby.

The invention claimed is:

1. Acetabular prosthesis comprising:
    an acetabular cup comprising an internal surface defining a coupling cavity and having a largest internal diameter,
    an insert able to be inserted inside said coupling cavity and comprising an external surface having a largest external diameter measured when in a disassembled condition,
    said acetabular cup and said insert having a common coupling axis and comprising respective clamping means for their reciprocal clamping in an assembled condition, wherein in the disassembled condition the largest internal diameter of the acetabular cup is less than the largest external diameter of said insert, and when in the assembled condition with the largest external diameter of the insert disposed within the acetabular cup the largest external diameter of said insert is equal to the largest internal diameter of the acetabular cup, wherein the internal diameter of the acetabular cup is considered in correspondence to a coupling plane between the acetabular cup and the insert defined along said coupling axis, wherein furthermore said clamping means comprise:
    a first clamping surface made on said internal surface of said acetabular cup,
    a second clamping surface made on said external surface of said insert, and cooperating with said first clamping surface,
    wherein said second clamping surface includes the largest external diameter of said insert,
    said first clamping surface and said second clamping surface having a truncated cone shape with an inclination different from each other with respect to said coupling axis, so as to obtain a conical coupling between said insert and said acetabular cup, with continuous but variable interference relative to said coupling axis; and
    wherein the largest external diameter of the insert is coincident with a maximum interference between the insert and the acetabular cup.

2. Acetabular prosthesis as in claim 1, wherein said variable interference, during use, is maximum in proximity to the maximum diameters of the cones, and minimum in proximity to the minimum diameters of the cones defining said first clamping surface and said second clamping surface, and further wherein, when in the assembled condition, the largest external diameter of said insert is coincident with a maximum interference and is disposed within the acetabular cup.

3. Acetabular prosthesis as in claim 1, wherein said first clamping surface has an inclination less than an inclination of said second clamping surface.

4. Acetabular prosthesis as in claim 1, wherein at least one of either said acetabular cup and said insert is made of ceramic material.

5. Acetabular prosthesis as in claim 1, wherein said acetabular cup is shaped so as to comprise a through aperture in correspondence to a polar region thereof.

6. Acetabular prosthesis as in claim 5, wherein said insert is shaped so as to comprise, in a polar region thereof, a centering element able to be inserted inside said through aperture.

7. Acetabular prosthesis as in claim 1, wherein said acetabular cup comprises a plurality of recesses able to position said acetabular prosthesis in an acetabular seating.

8. Acetabular prosthesis as in claim 1, wherein said acetabular cup comprises a trabecular reticular structure.

9. Acetabular prosthesis as in claim 8, wherein the trabecular reticular structure constitutes all or part of the acetabular cup.

10. Acetabular prosthesis as in claim 8, wherein at least part of the trabecular reticular structure is formed, without a break in continuity, by one or more models of a plurality of geometric meshes which are repeated in space on all the trabecular reticular structure, and have a cellular geometry with open and contiguous elementary cells, so as to define a plurality of polygons, with non-coplanar vertexes, with a spatial development delimiting cavities.

11. Acetabular prosthesis as in claim 8, wherein the trabecular reticular structure is obtained using Electronic Beam Melting (EBM) or Selective Laser Melting (SLM).

12. Method for assembling the acetabular prosthesis as in claim 1, comprising:
    providing the acetabular cup,
    providing the insert,
    coupling the acetabular and the insert along the common coupling axis and reciprocally clamping said acetabular cup and said insert in the assembled condition by means of the respective clamping means,
    providing the first clamping surface,
    providing the second clamping surface,
    obtaining the conical coupling between said insert and said acetabular cup, with variable interference along said coupling axis.

13. Method as in claim 12, wherein it comprises at least a step in which said acetabular cup is gripped by elastic gripping means in correspondence to a through aperture, a step in which said insert is positioned on a support and centering element, a step in which the elastic gripping means are moved and said acetabular cup is coupled through variable interference with said insert, making said first clamping surface and said second clamping surface cooperate with each other, and a step in which said elastic gripping means release said acetabular cup coupled with said insert.

14. Method as in claim 13, wherein it comprises a preliminary step of aligning and centering said elastic gripping means and said insert positioned on said support and centering element, moving said elastic gripping means downward.

15. Method as in claim 14, wherein, after the alignment and centering of said elastic gripping means and said insert, said elastic gripping means are lifted, said insert is removed from the support and centering element, said acetabular cup is placed on the support and centering element, the elastic gripping means are moved downward to grip the acetabular cup, the elastic gripping means associated with the acetabular cup are lifted and the insert is again positioned on the support and centering element in order to proceed with the conical coupling.

16. Method as in claim 13, wherein the assembly is obtained by applying a thermal load, or mechanically, or a combination of application of a thermal load and mechanical assembly.

17. Acetabular prosthesis as in claim 1, wherein:
the acetabular cup includes an external surface having an external ring formed adjacent an equatorial band and in proximity to the first and second clamping surfaces and the coupling plane; and
wherein the external ring includes a height, and wherein an overall rigidity of the acetabular cup can be increased by increasing the height of the external ring.

18. Acetabular prosthesis as in claim 1, wherein:
the largest external diameter of the insert is in direct contact with the largest internal diameter of the acetabular cup;
the acetabular cup has a polar region having a cylindrical through aperture; and
the insert includes a polar region having a cylindrical peg sized for insertion in the cylindrical through aperture.

19. Acetabular prosthesis comprising:
an acetabular cup comprising an internal surface defining a coupling cavity, the coupling cavity of the acetabular cup having a largest internal diameter;
an insert sized for insertion inside the coupling cavity and comprising an external surface and having a largest external diameter measured when in a disassembled condition;
the acetabular cup and the insert arranged for clamping to one another in an assembled condition and along a common coupling axis;
the insert and the acetabular cup arranged so that, in the disassembled condition, the largest internal diameter of the coupling cavity of the acetabular cup is less than the largest external diameter of the insert;
the insert and the acetabular cup further arranged so that, in the assembled condition, the largest external diameter of the insert is equal to the largest internal diameter of the coupling cavity of the acetabular cup, the largest external diameter of the insert and the largest internal diameter of the acetabular cup are in proximity to a coupling plane between the acetabular cup and the insert defined along said coupling axis, with the largest external diameter of the insert disposed within the acetabular cup;
wherein the internal surface of the coupling cavity of the acetabular cup includes a first clamping surface having a truncated conical shape having a first inclination;
wherein the external surface of the insert includes a second clamping surface having a truncated conical shape having a second inclination larger than the first inclination;
the first clamping surface cooperating with the second clamping surface when in the assembled condition so as to obtain an exclusively conical coupling between the insert and the acetabular cup, the conical coupling having a variable interference relative to the coupling axis; and
wherein the acetabular cup includes an external surface having an equatorial band shaped to comprise an external ring, and wherein all of the external ring is disposed above the coupling plane when in the assembled condition, and
wherein the largest external diameter of the insert is in direct contact with the largest internal diameter of the acetabular cup at a point of maximum interference adjacent the coupling plane, and a point of minimum interference is disposed above the external ring.

20. Acetabular prosthesis as in claim 19, wherein:
the acetabular cup has a polar region having a cylindrical through aperture, and the insert includes a polar region having a cylindrical peg sized for insertion in the cylindrical through aperture.

* * * * *